(12) United States Patent
Abys et al.

(10) Patent No.: US 6,542,232 B2
(45) Date of Patent: Apr. 1, 2003

(54) METHOD OF DETERMINING THE QUALITY OF HARD GOLD

(75) Inventors: Joseph A. Abys, Howell, NJ (US); Michael L. Ammerman, Howell, NJ (US); Alan Blair, Murray Hill, NJ (US); Edward J. Kudrak, Morganville, NJ (US); Chen Xu, New Providence, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 39 days.

(21) Appl. No.: 09/887,826

(22) Filed: Jun. 22, 2001

(65) Prior Publication Data

US 2002/0196436 A1 Dec. 26, 2002

(51) Int. Cl.[7] .............................. G01J 3/44; G01N 21/65
(52) U.S. Cl. .................................................... 356/301
(58) Field of Search .......................... 356/301; 200/262, 200/266; 427/189, 190

(56) References Cited

U.S. PATENT DOCUMENTS 3,620,839 A * 11/1971 Geckle et al. .............. 428/206
4,674,878 A * 6/1987 Vo-Dinh .................... 356/301

* cited by examiner

Primary Examiner—Mark A. Robinson
Assistant Examiner—Jesse Rowe
(74) Attorney, Agent, or Firm—Lowenstein Sandler, PC

(57) ABSTRACT

In accordance with the invention, the quality of hard gold is determined by Raman vibrational spectroscopy. A sample of the hard gold is provided, a monochromatic light beam is directed onto the sample, and the frequency and intensity of the light scattered by the sample is analyzed for the vibrational frequencies of polymer molecules. Scattering frequencies offset from the initial beam frequency by about 2132 $cm^{-1}$ and about 2182 $cm^{-1}$, for example, are indicative of high quality nickel-hardened gold.

5 Claims, 2 Drawing Sheets

METHOD OF DETERMINING THE QUALITY OF HARD GOLD

FIELD OF THE INVENTION

This invention relates to gold coatings and, in particular, to a method of determining the quality of a particular form of gold known as hard gold.

BACKGROUND OF THE INVENTION

Hard gold is a particular form of gold widely used in the electronics industry for electrical contact finishes of improved wear resistance. Hard gold is typically defined as gold containing 0.1 to 0.3 percent by weight of a transition metal such as cobalt or nickel. As compared to pure gold it has greater hardness (120–200 KHV vs. 60–90 KHV for pure gold). More importantly, the resistance of hard gold deposits to sliding wear is greatly superior to that of pure gold deposits.

Hard gold is typically deposited by electroplating from mildly acidic solutions in which the source of gold is potassium gold cyanide and the transition metal is present as a salt or complex. It has been demonstrated that the transition metal is incorporated into the hard gold deposit in two different forms: a metallic form and a non-metallic form, often referred to as "polymer". The polymer has been identified as transition metal cyanide compound and has been correlated with the improved wear behavior of hard gold.

While high quality hard gold provides remarkable wear resistance, quality control of hard gold deposits has proved very difficult. The conventional approach has been to measure the total concentration of the transition metal or the hardness of the plating. Unfortunately, neither of these measures is a good indication of the performance a hard gold contact. Efforts to detect and quantify the polymer have not been successful as a method of quality control. Accordingly there is a need for an improved method of determining the quality of Hard Gold.

SUMMARY OF THE INVENTION

In accordance with the invention, the quality of hard gold is determined by Raman vibrational spectroscopy. A sample of the hard gold is provided, a monochromatic light beam is directed onto the sample, and the frequency and intensity of the light scattered by the sample is analyzed for the vibrational frequencies of polymer molecules. Scattering frequencies offset from the initial beam frequency by about 2132 cm$^{-1}$ and about 2182 cm$^{-1}$, for example, are indicative of high quality nickel-hardened gold.

BRIEF DESCRIPTION OF THE DRAWINGS

The advantages, nature and various additional features of the invention will appear more fully upon consideration of the illustrative embodiments now to be described in detail in connection with the accompanying drawings. In the drawings.

It is to be understood that these drawings are for purposes of illustrating the concepts of the invention and, except for the graphs, are not to scale.

DETAILED DESCRIPTION

Figure 1:
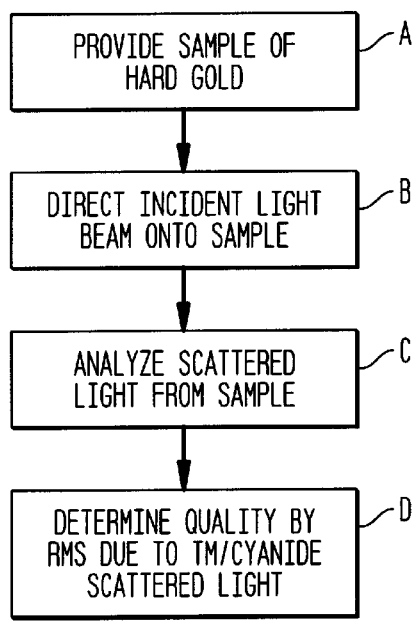
FIG. 1 is a schematic flow diagram showing the steps in determining the quality of hard gold in accordance with the invention.

Referring to the drawings, FIG. 1 is a flow diagram showing the steps in determining the quality of hard gold. The first step shown in Block A of FIG. 1 is to provide a sample of the gold to be tested. The sample can be gas, liquid or solid, and its form and size are largely irrelevant. The sample can even be microscopic (as small as $10^{-18}$m$^3$).

The next step, shown in Block B, is to direct a monochromatic laser beam onto the sample and to analyze the frequency and intensity of the light scattered by the sample. Most of the light scattered by the sample will be at the same frequency as the incident beam (Rayleigh scattered light). Some of the scattered light will be at different frequencies offset from the frequency of the incident beam (Raman scattered light).

Figure 2:
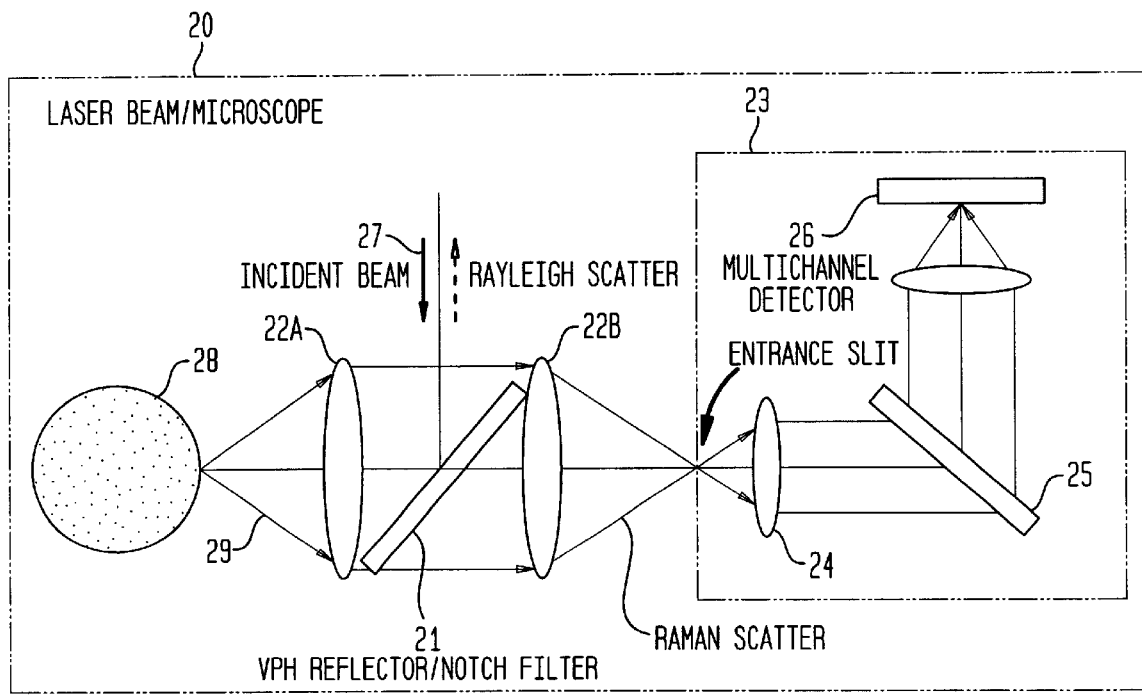
FIG. 2 is a schematic diagram of apparatus useful in practicing the method of FIG. 1.

FIG. 2 is a schematic diagram of a Raman spectrometer 20 useful for directing the beam and analyzing the scattered light. The spectrometer 20 comprises a volume phase holography ("VPH") reflector/notch filter 21 disposed between a collimating lens 22A and a focusing lens 22B. The VPH reflector/notch filter 21 reflects light at a chosen, precise frequency and allows other frequencies to be transmitted. Filter 21 reflects at precisely the frequency of the laser. The spectrometer 20 further comprises an analyzer 23 for detecting intensities at different frequencies comprising a collimating lens 24, a grating 25, and a multichannel detector 26.

In operation, monochromatic light 27 from a laser (not shown), reflects from filter 21 onto a gold sample 28. Light 29 scattered from the sample 28 returns to the filter 21. The scattered light which has not shifted in frequency (Rayleigh scatter) is reflected. The scattered light which has shifted in frequency (Raman scatter) is transmitted through filter 21 and enters the analyzer 23 where the intensities at different frequencies are measured.

The third step (Block C), is to evaluate the quality of the hard gold based on the spectral content of the Raman scattered light. The frequency shift between the incident beam and the Raman scattered light is associated with the characteristic vibrational frequency of molecules in the sample. Specifically, if $f_o$ is the frequency of the incident light and $f_s$ is the frequency of the Raman scatter, then the molecular vibrational frequencies are given by $\Delta f = f_o - f_s$.

Figure 3:
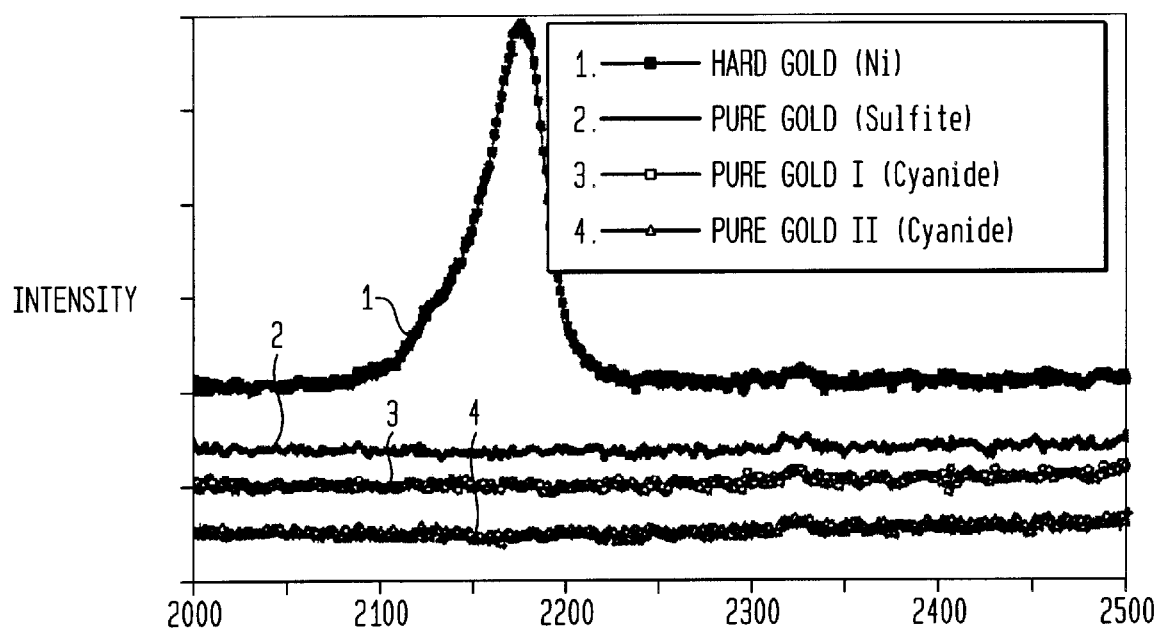
FIG. 3 is a graphical illustration showing the intensity versus offset frequency for hard gold and various pure gold deposits.

Applicants have found that hard gold is characterized by a significant peak at about 2180 cm$^{-1}$. FIG. 3 is a graphical illustration showing the intensity versus Raman offset frequency ($\Delta f$) for hard gold (curve 1) and various pure gold deposits (curves 2, 3 and 4). The hard gold shows a distinct peak whereas the pure gold deposits show only background noise.

Figure 4:
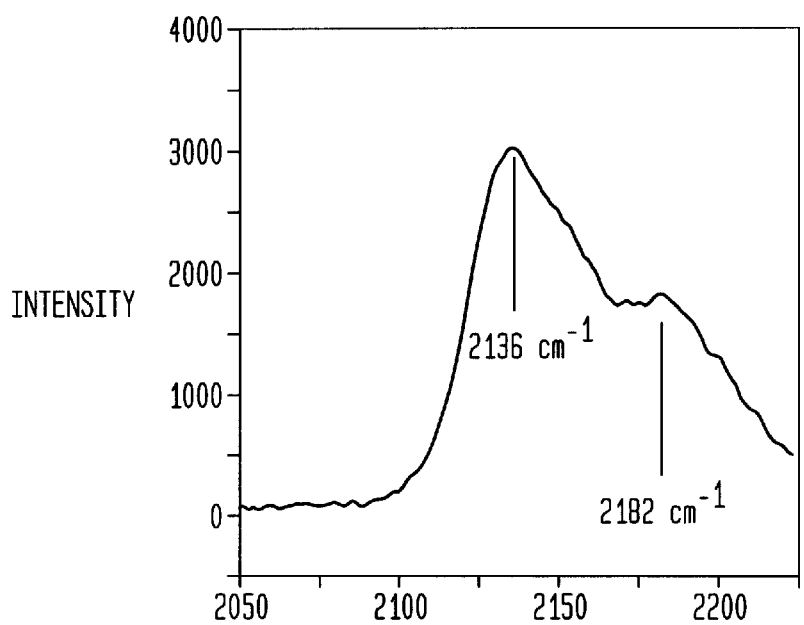
FIG. 4 is a graphical illustration at enlarged frequency scale showing the intensity versus offset frequency for nickel-hardened gold.

A higher resolution analysis of the hard gold Raman scatter for a nickel-hardened gold deposit is shown in FIG. 4. The single peak is resolved into two discrete peaks at 2132 cm$^{-1}$ and 2182 cm$^{-1}$. These two peaks are believed to correspond to stretching vibrations in transition metal cyanide compounds. The intensity of these peaks thus provides a measure of the content of these compounds and the quality of the hard gold.

It is to be understood that the above-described embodiments are illustrative of only a few of the many possible specific embodiments, which can represent applications of the principles of the invention. Numerous and varied other arrangements can be readily devised by those skilled in the art without departing from the spirit and scope of the invention.

What is claimed is:

1. A method of determining the quality of hard gold comprising the steps of:

providing a sample of hard gold;

directing an incident beam of light onto the sample;

analyzing the scattered light; and determining the quality of the hard gold in accordance with the intensity of Raman scattered light attributable to transition metal cyanide compounds.

2. The method of claim 1 wherein the beam of light comprises laser light.

3. The method of claim 1 wherein the beam of light comprises monochromatic laser light.

4. The method of claim 1 wherein the quality of the hard gold is determined in accordance with the intensity of Raman scattered light offset from the incident light by about 2182 cm$^{-1}$.

5. The method of claim 1 wherein the quality of the hard gold is determined in accordance with the intensity of Raman scattered light offset from the incident light by about 2132 cm$^{-1}$.

* * * * *